US012076717B2

(12) United States Patent
Lee et al.

(10) Patent No.: US 12,076,717 B2
(45) Date of Patent: Sep. 3, 2024

(54) METHOD FOR WASHING ION EXCHANGE RESIN AND METHOD FOR PREPARING BISPHENOL A

(71) Applicant: LG CHEM, LTD., Seoul (KR)

(72) Inventors: Sung Ho Lee, Daejeon (KR); Sang Beom Lee, Daejeon (KR); Joon Ho Shin, Daejeon (KR); In Yong Jeong, Daejeon (KR); Min Suk Kang, Daejeon (KR)

(73) Assignee: LG CHEM, LTD., Seoul (KR)

( * ) Notice: Subject to any disclaimer, the term of this patent is extended or adjusted under 35 U.S.C. 154(b) by 79 days.

(21) Appl. No.: 16/634,787

(22) PCT Filed: Jan. 22, 2019

(86) PCT No.: PCT/KR2019/000925
§ 371 (c)(1),
(2) Date: Jan. 28, 2020

(87) PCT Pub. No.: WO2019/156391
PCT Pub. Date: Aug. 15, 2019

(65) Prior Publication Data
US 2020/0206726 A1 Jul. 2, 2020

(30) Foreign Application Priority Data

Feb. 9, 2018 (KR) .................. 10-2018-0016530
Jan. 18, 2019 (KR) .................. 10-2019-0007108

(51) Int. Cl.
*B01J 47/016* (2017.01)
*B01J 39/04* (2017.01)
*C07C 37/20* (2006.01)
*C07C 37/82* (2006.01)
*C07C 37/84* (2006.01)
*C07C 39/16* (2006.01)

(52) U.S. Cl.
CPC ............. *B01J 47/016* (2017.01); *B01J 39/04* (2013.01); *C07C 37/20* (2013.01); *C07C 37/82* (2013.01); *C07C 37/84* (2013.01); *C07C 39/16* (2013.01)

(58) Field of Classification Search
CPC ......... C07C 37/84; C07C 37/20; C07C 37/82; C07C 39/16; C07C 37/88; B01J 47/016; B01J 39/04; B01J 39/20; B01J 49/60
See application file for complete search history.

(56) References Cited

U.S. PATENT DOCUMENTS

| 6,723,881 B1 | 4/2004 | Boediger et al. |
| 7,923,586 B2 * | 4/2011 | Stahlbush ............... C07C 37/20 568/728 |
| 2008/0319237 A1 | 12/2008 | Stahlbush et al. |
| 2011/0251438 A1 | 10/2011 | Muennich et al. |

FOREIGN PATENT DOCUMENTS

| CN | 1391499 A | 1/2003 | |
| CN | 101111314 A | 1/2008 | |
| CN | 101291899 A | 10/2008 | |
| EP | 1939164 A1 * | 7/2008 | ............. C07C 37/20 |
| JP | 9-173858 A | 7/1997 | |
| JP | H09-176069 A * | 7/1997 | ............. B01J 31/08 |
| JP | 2000-143565 A | 5/2000 | |
| JP | 2002-265403 A | 9/2002 | |
| JP | 3742440 B2 | 11/2005 | |
| JP | 3934707 B2 | 3/2007 | |
| JP | 2007-112762 A | 5/2007 | |
| KR | 10-2002-0048434 A | 6/2002 | |
| KR | 10-0698424 B1 | 3/2007 | |
| KR | 2008-0057303 A | 6/2008 | |
| KR | 2014-0108553 A | 9/2014 | |

OTHER PUBLICATIONS

Itochu (Chapter X, Other Use (https://web.archive.org/web/20161201000000*/http://www.itochu-purification.com/download/index/112, Dec. 2016, pp. 327-363) (Year: 2016).*
First Office Action issued in corresponding Chinese Patent Application No. 201980003769X, dated Jun. 20, 2022.
Search Report issued in corresponding Chinese Patent Application No. 201980003769X, dated Jun. 8, 2022.

\* cited by examiner

*Primary Examiner* — Rosalynd A Keys
(74) *Attorney, Agent, or Firm* — Morgan, Lewis & Bockius LLP

(57) ABSTRACT

A method of washing an ion exchange resin, including washing an ion exchange resin with deionized water (DI water) one or more times to prepare a washed ion exchange resin; and storing the washed ion exchange resin in dionized water. A method for producing bisphenol A using the method of washing an ion exchange resin. The resulting bisphenol A has improved purity, thermal stability, color, and the like.

13 Claims, No Drawings

METHOD FOR WASHING ION EXCHANGE RESIN AND METHOD FOR PREPARING BISPHENOL A

CROSS-REFERENCE TO RELATED APPLICATIONS

This application is the U.S. national stage of international application No. PCT/KR2019/000925, filed on Jan. 22, 2019, and claims benefit of priority to Korean Patent Application No. 10-2018-0016530, filed on Feb. 9, 2018, and Korean Patent Application No. 10-2019-0007108, filed on Jan. 18, 2019, the disclosures of which in their entirety are incorporated herein as a part of the specification.

TECHNICAL FIELD

The present invention relates to a method of washing an ion exchange resin and a method of producing bisphenol A using a washed ion exchange resin.

BACKGROUND

A bisphenol-A (BPA) is used as a raw material for producing a polycarbonate resin, a polyarylate resin, an epoxy resin, and the like. Bisphenol A is produced by reacting acetone with an excessive amount of phenol in the presence of an acid catalyst.

Conventionally, an inorganic mineral acid such as a sulfuric acid, a hydrochloric acid, or the like, has been used as an acid catalyst in the production of bisphenol A. However, in recent years, an ion exchange resin has received attention as the acid catalyst due to safety, selectivity, and the like. The ion exchange resin is produced by being swollen in water, thus contains moisture accounting for 45 wt % to 85 wt % based on the total weight.

However, since the ion exchange resin contains a high amount of moisture as described above, the ion exchange resin is unstable and easily deteriorated when being used as an acid catalyst in the production of bisphenol A. In addition, the ion exchange resin has a predetermined amount of an acidic monomolecular material or an acidic oligomer moiety in a production process of the ion exchange resin. The acidic monomolecular material or acidic oligomer moiety causes problems in that purity, thermal stability, color (transparency), and the like of bisphenol A are lowered. Specifically, when a sulfonic acid type cation exchange resin is used as an acid catalyst in the production of bisphenol A, a sulfonic acid, which is an acidic effluent, spills out from the cation exchange resin, and the spilled sulfonic acid reacts with iron and bisphenol A at a high temperature of 120° C. or higher, which is a process for producing bisphenol A, to produce a black solid sulfonic acid-containing heavy material. The solid sulfonic acid-containing heavy material as produced above acts as an impurity in bisphenol A, thereby lowering the purity, thermal stability, color, and the like of bisphenol A. Here, generation of the impurity is particularly accelerated in the presence of water.

Therefore, it is required to improve the purity, thermal stability, color, and the like of bisphenol A used as a raw material for a resin (for example, a polycarbonate resin) for which demand for optical use is increasing, in addition to improvement of the ion exchange resins used as acid catalysts.

SUMMARY

An object of the present invention is to provide a method of washing an ion exchange resin capable of minimizing spill of an acidic effluent of the ion exchange resin during a method of producing bisphenol A.

Another object of the present invention is to provide a method of producing bisphenol A capable of improving purity, thermal stability, color, and the like of bisphenol A, using the ion exchange resin washed by the above-described washing method as an acid catalyst at the time of producing bisphenol A.

In one general aspect, a method of washing an ion exchange resin includes: washing an ion exchange resin with deionized water (DI water) one or more times (S10); and adding the washed ion exchange resin to the deionized water and storing the ion exchange resin at 38° C. or more for 6 hours or more (S20).

In another general aspect, a method of producing bisphenol A includes: reacting phenol and acetone in the presence of an ion exchange resin washed with the washing method as described above to obtain a reaction product (S100); and crystallizing and solid-liquid separating the reaction product to obtain an adduct including bisphenol A (S200).

The present invention may minimize an amount of an acidic effluent included in an ion exchange resin since the ion exchange resin is washed through continuous treatment with deionized water (DI water) and through storage at a high temperature. Further, since bisphenol A is produced using the ion exchange resin of which an amount of the acidic effluent is minimized, the present invention may provide bisphenol A having improved purity, thermal stability, color (transparency), and the like.

DETAILED DESCRIPTION

Terms and words used in the present specification and claims are not to be construed as a general or dictionary meaning but are to be construed as meanings and concepts meeting the technical ideas of the present invention based on a principle that the inventors can appropriately define the concepts of terms in order to describe their own inventions in the best mode.

Hereinafter, the present invention is described.

Bisphenol A (BPA) is produced by reacting acetone with an excessive amount of phenol in the presence of an acid catalyst. As the acid catalyst, an ion exchange resin has received attention, and the ion exchange resin is also used industrially.

However, the ion exchange resin contains an acidic effluent such as residual sulfonic acid, and is produced in a swollen state in water, which is unstable, and is easily degraded. Specifically, a problem such as degradation, deterioration, or the like of the ion exchange resin is likely to occur in storage or transportation of the ion exchange resin used as the acid catalyst by the acidic effluents and moisture. In particular, the acidic effluents such as residual sulfonic acid may deteriorate the color of bisphenol A.

Therefore, before the ion exchange resin is used as a catalyst for a condensation reaction of phenols and ketones, the ion exchange resin is subjected to a washing process of removing by-products that remain in the production of the ion exchange resin, additional materials that may be generated immediately after the production of the ion exchange resin, and additional materials generated by spontaneous decomposition of the ion exchange resin, and a dehydration process of dehydrating water included in the ion exchange resin.

As the process of washing the ion exchange resin, conventionally, a method in which the ion exchange resin is washed by continuous backwashing with deionized water (DI water), and then the washing is terminated when electrical conductivity and activity of the deionized water used for washing are decreased below a predetermined value has been used. However, the acidic effluent included in the ion exchange resin is not capable of being sufficiently removed by the continuous washing (cleaning) using the DI water as described above. Thus, bisphenol A is produced by using the ion exchange resin in which the acidic effluent is not sufficiently removed, causing a problem in that the color of bisphenol A is lowered.

In order to solve these conventional problems, according to the washing method of the present invention, the ion exchange resin is continuously washed with the DI water, and then the ion exchange resin added in the DI water is stored at a predetermined temperature for a predetermined time. When the ion exchange resin is washed by the washing method of the present invention, the acidic effluent re-spilling from the ion exchange resin may be sufficiently removed after the continuous washing using the DI water, and thus an amount of the acid effluent remaining in the ion exchange resin may be significantly reduced.

That is, the method of washing an ion exchange resin according to the present invention may include washing an ion exchange resin with deionized water (DI water) one or more times (S10); and adding the washed ion exchange resin to the deionized water and storing the ion exchange resin at 38° C. or more for 6 hours or more (S20).

According to an embodiment of the present invention, step (S10) may be a step of continuously washing the ion exchange resin with deionized water. The washing with the deionized water may be performed one or more times, two to ten times, or two to eight times.

Specifically, according to an embodiment of the present invention, step (S10) may be repeatedly performed while replacing the deionized water until the pH of the deionized water discharged after washing the ion exchange resin becomes 6.2 to 7 (for example, neutral). For example, in step (S10), the ion exchange resin is added to deionized water to perform a first washing (first washing with deionized water), and then when the pH of the deionized water used for the first washing is measured as being out of the range of 6.2 to 7, the deionized water is newly replaced. Next, the ion exchange resin is added to the replaced deionized water to perform a second washing (second washing with deionized water), and then in a case where the pH is out of the range of 6.2 to 7 when the pH of the deionized water used for the second washing is measured, the deionized water is newly replaced. Then, the ion exchange resin is added to the replaced deionized water to perform a third washing (third washing with deionized water), and then in a case where the pH is within the range of 6.2 to 7 when the pH of the deionized water used for the third washing is measured, a step (S20) described below proceeds.

According to an embodiment of the present invention, the washing process of step (S10) may be performed at about 0° C. to 80° C. about 10° C. to 30° C. or at room temperature (about 25° C.). As the washing process of the ion exchange resin is performed within the temperature range, the acidic effluent included in the ion exchange resin may be efficiently washed without consuming any thermal energy in the washing process.

The acidic effluent may still be included in the ion exchange resin washed in step (S10). Accordingly, the washing method according to the present invention may include storing the ion exchange resin washed in step (S10) in the deionized water so as to minimize an amount of the acidic effluent remaining in the ion exchange resin (S20).

Specifically, according to an embodiment of the present invention, step S20 may be a step of further removing the acidic effluent by re-spilling the acidic effluent in the ion exchange resin which is not removed in step (S10). A temperature at which the deionized water to which the ion exchange resin is added is stored may be 38° C. or higher, 50° C. or higher, or 50° C. to 90° C. In addition, the time for storing the deionized water to which the ion exchange resin is added may be 6 hours or more, 6 hours to 30 hours, or 6 hours to 20 hours. As the deionized water to which the ion exchange resin is added is stored within the ranges of the temperature and the time, the spill (elution) of the acidic effluent included in the ion exchange resin may be smoothly performed, thereby minimizing the amount of the acidic effluent included in the ion exchange resin.

According to an embodiment of the present invention, a used amount of the deionized water to which the ion exchange resin is added in step (S20) may be 1.5 times or more, 1.6 times or more, or 1.6 times to 1.8 times the weight of the ion exchange resin in step (S20). When the used amount of the deionized water is within the above-described range, the spill of the acidic effluent included in the ion exchange resin may be smoothly performed and a loss of the deionized water may be minimized during the washing process.

In addition, according to another embodiment of the present invention, steps (S10) and (S20) may be repeated one or more times, two or more times, or three to five times. For example, step (S20) may be performed through step (S10) (first performed), step (S20) may be performed through step (S10) (second performance), and step (S20) may be performed through step (S10) (third performance). By repeatedly performing the washing process including both steps (S10 and S20) one or more times, the amount of the acidic effluent included in the ion exchange resin may be minimized, thereby improving color characteristics of bisphenol A.

Specifically, according to an embodiment of the present invention, step (S10) and step (S20) may be repeatedly performed while replacing the deionized water until a concentration of the acidic effluent of the deionized water discharged in step (S20) is 0.5 ppm or less, 0.4 ppm or less, or 0.3 ppm to 0.1 ppm. That is, the acidic effluent included in the ion exchange resin is spilled out into the deionized water by performing step (S10) and step (S20), wherein the washing process including both steps (S10 and S20) is repeated until the concentration of the acidic effluent included in the deionized water spilled out in step (S20) becomes 0.5 ppm or less. For example, step (S10) and step (S20) are performed, respectively, and then when the concentration of the acidic effluent of the deionized water discharged in step (S20) is measured as more than 0.5 ppm, the deionized water is newly replaced, and step (S10) and step (S20) are performed again, respectively. Next, step (S10) and step (S20) are performed again, respectively, and then when the concentration of the acidic effluent of the deionized water discharged in step (S20) is measured as more than 0.5 ppm, the deionized water is newly replaced, and step (S10) and step (S20) are performed again, respectively. Then, step (S10) and step (S20) are performed again, respectively, and then when the concentration of the acidic effluent of the deionized water discharged in step (S20) is measured as 0.5 ppm or less, repeatedly performed steps (S10 and S20) are terminated. When bisphenol A is produced using the ion exchange resin that is washed until the concentration of the acidic effluent of the deionized water discharged in step (S20) becomes 0.5 ppm or less, oxidation of bisphenol A due to the acidic effluent in the method of producing bisphenol A is minimized, and thus bisphenol A having improved color characteristics may be produced.

Specifically, according to the present invention, the ion exchange resin is washed until the acidic effluent, which is a direct cause of color degradation in the production of bisphenol A, is included into the deionized water (deionized water discharged after washing) below a predetermined concentration (i.e., a concentration at which generation of impurities is minimized or is not induced in the production of bisphenol A), and thus the acidic effluent included in the ion exchange resin may be removed more efficiently as compared to the conventional washing method of simply washing the ion exchange resin until electrical conductivity and activity of the deionized water become a predetermined value or less.

According to an embodiment of the present invention, the acidic effluent may refer to an acidic material spilled out from the ion exchange resin. Specifically, the acidic effluent may include at least one selected from the group consisting of sulfonic acid, phenol sulfonic acid, sulfobenzoic acid, formyl benzenesulfonic acid, acetyl benzenesulfonic acid, and a sulfonic acid group-containing organic acid. Here, the sulfonic acid may be a material performing a catalytic action such as decomposition of bisphenol A into phenol and isopropenylphenol under high temperature conditions, formation of impurities, or the like.

According to an embodiment of the present invention, as described above, in performing step (S10) and step (S20), respectively, the step of repeatedly washing or storing the ion exchange resin may be performed while the deionized water is newly replaced. That is, after the washing process in step S10, the deionized water used in the storing process in step S20 is replaced with fresh deionized water, and after the storing process in step S20, the deionized water used in the continuous washing process in step S10 may be replaced with fresh deionized water.

Meanwhile, according to an embodiment of the present invention, the washing method may further include storing the ion exchange resin in phenol, followed by dehydrating and drying (S30) in order to minimize moisture included in the ion exchange resin. When the ion exchange resin includes a high amount of moisture, the ion exchange resin may be degraded or deteriorated during storage or transportation, and an activity of the ion exchange resin may be lowered. In addition, since the ion exchange resin serves as a catalyst, the reaction rate of phenols and ketones may also be affected. Thus, moisture included in the ion exchange resin is sufficiently removed by performing step (S30).

Step S30 may be performed after step (S10) and step (S20). Specifically, step (S30) may be performed by storing the ion exchange resin, which is produced after performing steps (S10) and (S20), in a predetermined amount of phenol for 1 hour or more, or for 1 hour to 3 hours and then removing phenol. Here, a percentage of moisture content of the phenol discharged in step (S30) may be about 4 wt % or less, about 2 wt % or less, or less than about 1 wt %, based on the total weight of the phenol. Since the percentage of moisture content of the phenol discharged in step (S30) is about 4 wt % or less, the ion exchange resin may obtain the reaction rate limit of serving as a catalyst. Step (S30) may be repeated three or more times while replacing the phenol.

According to an embodiment of the present invention, the ion exchange resin may be a cation exchange resin, and specifically, a sulfonic acid type cation exchange resin. Here, the sulfonic acid type cation exchange resin may be a gel-like or porous sulfonated polystyrene resin (acid ion exchanger) containing divinylbenzene as a cross-linking agent.

The ion exchange resin washed with the washing method of the present invention as described above may be usefully used as an acid catalyst in the process of producing bisphenol A by a condensation reaction of phenol and acetone since the amount of the acidic effluent is minimized.

The present invention provides a method of producing bisphenol A using an ion exchange resin washed by the method of washing the ion exchange resin described above. That is, the method of producing bisphenol A according to the present invention may include reacting phenol and acetone in the presence of an ion exchange resin washed with the washing method as described above to obtain a reaction product (S100); and crystallizing and solid-liquid separating the reaction product to obtain an adduct including bisphenol A (S200).

According to an embodiment of the present invention, step (S100) may be performed by a condensation reaction of phenol and acetone in a reactor using the ion exchange resin as an acid catalyst. Here, a reaction ratio of phenol to acetone may be a molar ratio of 5 to 13:1. In addition, a temperature for the condensation reaction may be 45° C. to 110° C., 50° C. to 105° C., 55° C. to 100° C., or 58° C. to 90° C. This condensation reaction may be performed continuously by passing phenol and acetone through the reactor. By the condensation reaction, a reaction product (reaction mixture) including bisphenol A, water, unreacted phenol, unreacted acetone, and by-products may be obtained.

The by-products included in the reaction product obtained in step (S100) may be 2-(4-hydroxyphenyl)-2-(2-hydroxyphenyl)propane (o, p-BPA), indane substituted with a hydrocarbon group having 1 to 30 carbon atoms, hydroxyphenyl indanol, hydroxyphenyl chroman, spirobis(indane), indenol substituted with a hydrocarbon group having 1 to 30 carbon atoms, xanthene substituted with a hydrocarbon group having 1 to 30 carbon atoms, or a condensed compound having three or more phenyl rings in a molecular skeleton. Further, the by-products may also include anisol, mesityl oxide, mesitylene, diacetone alcohol, or the like, which is formed as results of natural condensation of acetone and reaction with impurities among raw materials. In addition to the by-products, water, unreacted phenol, and unreacted acetone may have a harmful effect upon the production of bisphenol A, and thus a separation (removing) process from the reaction product may be performed.

According to an embodiment of the present invention, the condensation reaction of the phenol with the acetone may be performed using a vertical fixed bed reactor or a mobile phase reactor in which the above-described ion exchange resin is filled with an acid catalyst.

Further, according to an embodiment of the present invention, in addition to the above-described acid catalyst, a mercaptan, which is a thiol-based compound, may be used as a cocatalyst. Specifically, the acid catalyst may be a sulfonic acid type cation exchange resin to which the mercaptan is bonded as the cocatalyst. Here, the mercaptan may be methyl mercaptan or ethyl mercaptan.

Meanwhile, according to an embodiment of the present invention, the reaction product obtained in step (S100) may be concentrated and obtained in the form of a concentrate. The concentrate is a stream including a reaction product obtained by reacting phenol with acetone, which may indicate that water, acetone, phenol or other highly volatile components discharged from the reactor are completely or partially removed by distillation. Specifically, the reaction product may be concentrated through a first concentration step and a second concentration step.

The first concentration step may be performed by a method such as distillation under reduced pressure or the like. The distillation under reduced pressure may be performed at a temperature of 30 to 180° C. and a pressure of 13 kPa to 67 kPa. Through this first concentration step, acetone, water (water generated in reaction), and the like may be removed. The reaction product in the form of a concentrate obtained in the first concentration step may include 30 to 80 wt % of bisphenol A, 1 to 60 wt % of phenol, and 5 to 40 wt % of by-products, based on the total weight of the reaction product.

The second concentration step may be performed by a method such as distillation under reduced pressure or the like. The distillation under reduced pressure may be performed at a temperature of 70 to 140° C. and a pressure of 4 kPa to 40 kPa. Through this second concentration process, the concentration of the reaction product may be controlled by partially removing phenol and the like.

The concentration of bisphenol A included in the reaction product may be controlled through the first and second concentration processes. Specifically, the reaction product in the form of a concentrate obtained by the second concentration step may include 20 to 80 wt % of bisphenol A, 15 to 45 wt % of phenol, and 5 to 25 wt % of by-products, based on the total weight of the reaction product. Within this range, the yield of bisphenol A may be increased, and solidification may be prevented, and thus the reaction product may be easily transported.

According to an embodiment of the present invention, step (S200) may be performed by crystallizing and solid-liquid separating the reaction product in the form of a concentrate to obtain an adduct including bisphenol A.

The crystallization performed in step (S200) may be a cooling process. The cooling process is to continuously remove heat from the reaction product in the form of a concentrate containing bisphenol A and phenol in one or more coolers, which causes supersaturation. Through the cooling process, crystals including bisphenol A and phenol may be obtained. For example, the reaction product in the form of a concentrate may be cooled up to 35° C. to 60° C. from 70° C. to 140° C. thereby forming crystals including bisphenol A and phenol. Here, the cooling may be performed by heat removal due to latent heat by evaporation of water or hydrocarbons having a low boiling point applied to an external heat exchanger or crystallizer. In the cooling process for crystallization, in addition to the cooler, a residence time necessary for supersaturation decay and subsequent crystallization may be provided. Crystals including bisphenol A and phenol obtained by this process may be in the form of a suspension. Crystals in the form of a suspension as described above may be circulated through the cooler by a pump in the cooling process for crystallization.

The solid-liquid separation in step (S200) may be a step of separating the crystals in the form of a suspension including bisphenol A and phenol into a solid-liquid. The solid-liquid separation is performed using a solid-liquid separator. As the solid-liquid separator, a rotary filter or a centrifugal separator may be used.

According to an embodiment of the present invention, a solid component (adduct filtered and deposited on a filter surface of the solid-liquid separator) for obtaining bisphenol A obtained through the solid-liquid separator may be washed by a washing liquid. As the washing liquid, phenol recovered through distillation, raw phenol, water, a water-phenol mixture, a saturated phenol solution of bisphenol A, or the like may be used. As a used amount of the washing liquid is larger, a washing efficiency is better. However, in consideration of a redissolution loss of the adduct, and circulation, recovery and reuse of the washing liquid, the used amount of the washing liquid may be 0.1 to 10 times the weight of the crystals including bisphenol A and phenol.

By this washing process, the adduct including bisphenol A may be obtained. Here, in order to increase purity of the adduct, the adduct obtained by crystallization and solid-liquid separation may be redissolved, followed by repeated crystallization and solid-liquid separation. Here, the adduct may refer to crystals in a solid state in which bisphenol A and phenol are precipitated in a molar equivalent ratio of 1:1.

According to an embodiment of the present invention, the adduct including bisphenol A obtained through step (S200) may have a platinum-cobalt color (Pt—Co color of 50 or less, 45 or less, or 44 to 20 when measuring the color with a platinum-cobalt visual comparison method. Here, the measurement of the color of the adduct using the platinum-cobalt method may be performed after the adduct is exposed to the air at 170° C. for 1 hour. The platinum-cobalt color of the adduct may be 50 or less, and thus it is possible to provide bisphenol A having improved color characteristics (transparency).

Meanwhile, a liquid component (mother liquid) obtained through the crystallization and solid-liquid separation may be recycled to the condensation reaction or the concentration process. The liquid component (mother liquor) obtained through the crystallization and solid-liquid separation may include, based on the total weight of the liquid component, from 65 wt % to 85 wt % of phenol, from 10 wt % to 20 wt % of bisphenol A, 5 wt % to 15 wt % of by-products such as 2,4'-isomers, and the like.

According to an embodiment of the present invention, the adduct obtained through step (S200) may be subjected to decomposition and cooling processes for obtaining bisphenol A. Specifically, the adduct may be decomposed at the temperature of 100° C. to 160° C. to obtain a melt liquid including bisphenol A and phenol. Then, the melt liquid may be added to an evaporator to remove most of the phenol, followed by steam stripping so as to remove the remaining phenol, thereby obtaining a bisphenol A melt. Thereafter, the obtained bisphenol A melt may be cooled through a cooler to obtain particulate bisphenol A, which is called prill, from the column bottom.

As described above, according to the present invention, the ion exchange resin in which the amount of the acidic effluent is minimized through the washing method as described above is used as the acid catalyst in producing bisphenol A, it is possible to produce bisphenol A having excellent color characteristics, purity, and thermal stability.

Hereinafter, the present invention is described in more detail by explaining Examples. It is obvious to those skilled in the art, however, that the following Examples are illustrative of the present invention and that various changes and modifications can be made within the scope and spirit of the invention, and thus the scope of the present invention is not limited thereto.

Example 1

50 g of a cation exchange resin (polystyrene resin) was added to 85 g of deionized water (DI water) at room temperature, and the cation exchange resin was washed once by allowing the cation exchange resin to stand at room temperature for 30 minutes. After the washing once, in order to confirm that the pH of the deionized water was within the range of 6.2 to 7, the pH of the deionized water was measured with a pH meter (SevenCompact pH meter S210 manufactured by Mettler Toledo). Since the measured pH was out of the range of 6.2 to 7, the deionized water was replaced with a fresh deionized water, and then the cation exchange resin was washed again in the same manner as the first washing. The cation exchange resin was washed five times in total while the deionized water was replaced with fresh deionized water. As a result, the pH of the deionized water after washing was measured within the range of 6.2 to 7.

Then, 50 g of the cation exchange resin washed five times was added to 85 g of fresh deionized water and stored in an oven at 50° C. for 6 hours. Then, the deionized water was removed to complete the washing of the cation exchange resin.

Example 2

The washing of the cation exchange resin was completed by performing the same procedure as in Example 1 except that the cation exchange resin added in the deionized water was stored in an oven at 50° C. for 20 hours in the storing step of the cation exchange resin of Example 1.

Example 3

The washing of the cation exchange resin was completed by performing the same procedure as in Example 1 except that the cation exchange resin added in the deionized water was stored in an oven at 60° C. for 6 hours in the storing step of the cation exchange resin of Example 1.

Example 4

The washing of the cation exchange resin was completed by performing the same procedure as in Example 1 except that the cation exchange resin added in the deionized water was stored in an oven at 60° C. for 20 hours in the storing step of the cation exchange resin of Example 1.

Comparative Example 1

The washing of the cation exchange resin was completed by performing the same procedure as in Example 1 except that the cation exchange resin added in the deionized water was stored in an oven at 25° C. for 3 hours in the storing step of the cation exchange resin of Example 1.

Comparative Example 2

The washing of the cation exchange resin was completed by performing the same procedure as in Example 1 except that the cation exchange resin added in the deionized water was stored in an oven at 25° C. for 6 hours in the storing step of the cation exchange resin of Example 1.

Comparative Example 3

The washing of the cation exchange resin was completed by performing the same procedure as in Example 1 except that the cation exchange resin added in the deionized water was stored in an oven at 25° C. for 20 hours in the storing step of the cation exchange resin of Example 1.

Comparative Example 4

The washing of the cation exchange resin was completed by performing the same procedure as in Example 1 except that the cation exchange resin added in the deionized water was stored in an oven at 50° C. for 3 hours in the storing step of the cation exchange resin of Example 1.

Comparative Example 5

The washing of the cation exchange resin was completed by performing the same procedure as in Example 1 except that the cation exchange resin added in the deionized water was stored in an oven at 60° C. for 3 hours in the storing step of the cation exchange resin of Example 1.

Experimental Example 1

In Examples 1 to 4 and Comparative Examples 1 to 5, the pH of the deionized water discharged by the storing step of the cation exchange resin was measured with a pH meter (SevenCompact pH meter S210 manufactured by Mettler Toledo), and measurement results thereof are shown in Table 1 below.

TABLE 1

| Classification | Storage Temperature | Storage Time | pH |
| --- | --- | --- | --- |
| Example 1 | 50° C. | 6 hours | 4.29 |
| Example 2 | 50° C. | 20 hours | 4.23 |
| Example 3 | 60° C. | 6 hours | 4.19 |
| Example 4 | 60° C. | 20 hours | 4.18 |
| Comparative Example 1 | 25° C. | 3 hours | 6.2 |
| Comparative Example 2 | 25° C. | 6 hours | 6.01 |
| Comparative Example 3 | 25° C. | 20 hours | 5.51 |
| Comparative Example 4 | 50° C. | 3 hours | 4.60 |
| Comparative Example 5 | 60° C. | 3 hours | 4.51 |

Referring to Table 1, it could be confirmed that by washing the cation exchange resin using the washing method according to the present invention, the pH of the deionized water discharged from the storing step was measured to be low. This low pH measurement could be considered as a result of the fact that the acidic effluent included in the cation exchange resin was sufficiently spilled with deionized water. In particular, it could be appreciated that when the storage temperature was 50° C. or more, the pH of the deionized water was rapidly lowered, and thus a spill rate of the acidic effluent was increased. Further, it could be appreciated that the pH of the deionized water was constantly measured when the storage time was 6 hours or more.

On the other hand, in Comparative Examples 1 to 3 where the storage temperature was less than 30° C., it could be confirmed that the pH of the deionized water was high, and thus the spill of the acidic effluent included in the cation exchange resin was not sufficiently achieved. Further, referring to Comparative Examples 4 and 5, it could be confirmed that even though the storage temperature was adjusted to be 30° C. or more, since the storage time was less than 6 hours, the pH of the deionized water was measured to be high, and thus the spill of the acidic effluent included in the cation exchange resin was not sufficiently achieved.

Example 5

50 g of a cation exchange resin (polystyrene resin) was added to 85 g of deionized water (DI water) at room temperature, and the cation exchange resin was washed once by allowing the cation exchange resin to stand at room temperature for 30 minutes. After the washing once, in order to confirm that the pH of the deionized water was within the range of 6.2 to 7, the pH of the deionized water after the washing once was measured with a pH meter (SevenCompact pH meter S210 manufactured by Mettler Toledo). Since the measured pH was out of the range of 6.2 to 7, the deionized water was replaced with fresh deionized water, and then the cation exchange resin was subjected to second washing by allowing the cation exchange resin to stand at room temperature for 30 minutes. After the second washing, in order to confirm that the pH of the deionized water was within the range of 6.2 to 7, the pH of the deionized water after the second washing was measured with a pH meter. As a result of the measurement, the pH of the deionized water was confirmed to be within the range of 6.2 to 7.

50 g of the cation exchange resin washed 2 times was added to 85 g of fresh deionized water, and stored in an oven at 60° C. for 6 hours.

The washing and storing steps were repeated 2 times (the number of times of washing with deionized water: 4 times, the number of times of storing deionized water: 2 times), and then the pH of the deionized water discharged from the storing step was measured with a pH meter. As a result of the measurement, the pH of the deionized water was 6.4.

The deionized water was removed from the cation exchange resin after performing the washing and storing steps, and then the cation exchange resin was added to 200 g of phenol and stored at 60° C. for 1 hour and 30 minutes.

The storing step in phenol was repeated three times (performed by replacing phenol with fresh phenol), and a phenol removing process (dehydration and drying) was then performed to complete the washing of the cation exchange resin.

Example 6

The washing of the cation exchange resin was completed by performing the same procedure as in Example 5 except that the washing and storing steps of the cation exchange resin were repeated 3 times (the number of times of washing with deionized water: 6 times, and the number of times of storing deionized water: 3 times). As a result of repeating the above washing and storing steps three times, the pH of the deionized water discharged from the storing step was measured to be 6.6.

Comparative Example 6

50 g of a cation exchange resin (polystyrene resin) was added to 85 g of DI water at room temperature, and the cation exchange resin was washed once by allowing the cation exchange resin to stand at room temperature for 30 minutes. After the washing once, in order to confirm that the pH of the deionized water was within the range of 6.2 to 7, the pH of the deionized water after washing once was measured with a pH meter. Since the measured pH was out of the range of 6.2 to 7, the deionized water was replaced with fresh deionized water, and then the cation exchange resin was subjected to second washing by allowing the cation exchange resin to stand at room temperature for 30 minutes. After the second washing, in order to confirm that the pH of the deionized water was within the range of 6.2 to 7, the pH of the deionized water after the second washing was measured with a pH meter. As a result of the measurement, the pH of the deionized water was confirmed to be within the range of 6.2 to 7.

After the deionized water was removed from the cation exchange resin washed twice, the cation exchange resin was added to 200 g of phenol and stored at 60° C. for 1 hour and 30 minutes.

The storing step in phenol was repeated three times (performed by replacing phenol with fresh phenol), and a phenol removing process (dehydration and drying) was then performed to complete the washing of the cation exchange resin.

Experimental Example 2

Bisphenol A was produced using the cation exchange resin washed in each of Examples 5 to 6 and Comparative Example 6, and the degree of improvement in a color of bisphenol A was evaluated by determining the color of the adduct in a solid state obtained in the production process.

Specifically, phenol and acetone were added in a molar ratio of 10:1 to a reactor added with the cation exchange resin washed in each of Examples 5 to 6 and Comparative Example 6, and reacted continuously at 80° C. to obtain a reaction product. Next, a part of acetone, water, and phenol was vaporized from the reaction product to obtain a concentrate, and the concentrate was added to a crystallizer to obtain an adduct crystal suspension including bisphenol A and phenol. Then, the suspension was added to a solid-liquid separator and subjected to solid-liquid separation to obtain a solid adduct including bisphenol A and phenol. Next, the phenol was removed from the obtained solid adduct to obtain bisphenol A.

In order to evaluate the degree of improvement in a color of bisphenol A as obtained above, the color of the obtained adduct was measured by a platinum-cobalt visual comparison method. Results thereof are shown in Table 2 below. Specifically, the adduct was exposed to the air at 170° C. for 1 hour, and then the methanol and the adduct were mixed in a weight ratio of 0.4:1 to prepare a mixture. Next, the platinum-cobalt (Pt—Co) color of the prepared mixture was measured using a Tintometer AF325 apparatus.

Meanwhile, the platinum-cobalt (Pt—Co) color of phenol was measured as a reference. Specifically, pure phenol was exposed to the air at 170° C. for 1 hour and mixed with methanol in a weight ratio of 0.4:1, and the platinum-cobalt (Pt—Co) color was measured using a Tintometer AF325 apparatus. As a result, the platinum-cobalt (Pt—Co) color of pure phenol was confirmed to be 17.

TABLE 2

| Classification | Example 5 | Example 6 | Comparative Example 6 |
|---|---|---|---|
| Pt—Co color | 44 | 22 | 52 |

Referring to Table 2, it could be confirmed that when bisphenol A was produced using the cation exchange resin washed with the washing method according to the present invention, the Pt—Co color of the adduct obtained in the process of producing bisphenol A had a low value of 50 or less.

Here, as the value of the Pt—Co color of the adduct is smaller, the color of the adduct is more colorless and transparent. Further, on the basis that the platinum-cobalt (Pt—Co) color measured under the same condition in the case of the pure phenol was 17, the adduct obtained by the present invention had a low Pt—Co color of 50 or less, and thus it was predicted that bisphenol A of the present invention separated from the adduct would have an improved color characteristic.

On the other hand, it could be confirmed that in Comparative Example 6 in which the cation exchange resin added to the deionized water was not stored in deionized water, the Pt—Co color of the adduct had a high value of 50 or more. It was predicted that when bisphenol A was produced from the cation exchange resin of Comparative Example 6, the purity, thermal stability, and color quality of bisphenol A produced from the cation exchange resin of Comparative Example 6 would be significantly lower than those of bisphenol A obtained by the present invention.

Although specific embodiments of the present disclosure are described in detail, it will be apparent to those skilled in the art that the specific description is merely desirable exemplary embodiment and should not be construed as limiting the scope of the present disclosure. Therefore, the substantial scope of the present disclosure is defined by the accompanying claims and equivalent thereof.

The invention claimed is:

1. A method of washing an ion exchange resin, the method comprising:
   washing the ion exchange resin with deionized water (DI water) one or more times until a pH of the deionized water discharged after the washing is 6.2 to 7.0 to prepare a washed ion exchange resin; and
   storing the washed ion exchange resin in the deionized water, wherein a temperature of the storing of the washed ion exchange resin is 50° C. to 60° C. and a time of the storing of the washed ion exchange resin is 6 hours to 20 hours, and an amount of the deionized water to which the washed ion exchange resin is added is at a weight ratio of 1.6 times to 1.8 times based on a weight of the ion exchange resin,
   wherein the washing of the ion exchange resin and the storing of the washed ion exchange resin are performed repeatedly while replacing the deionized water until a concentration of an acidic effluent of the deionized water discharged immediately after the storing of the washed ion exchange resin is 0.5 ppm or less, and
   wherein the acidic effluent includes at least one selected from the group consisting of sulfonic acid, phenol sulfonic acid, sulfobenzoic acid, formyl benzenesulfonic acid, acetyl benzenesulfonic acid, and a sulfonic acid group-containing organic acid.

2. The method of claim 1, wherein the ion exchange resin is a cation exchange resin.

3. A method of producing bisphenol A, the method comprising:
   reacting phenol and acetone in the presence of the ion exchange resin washed with the method according to claim 1 to obtain a reaction product; and
   crystallizing and solid-liquid separating the reaction product to obtain an adduct including bisphenol A.

4. The method of claim 3, wherein the adduct has a platinum-cobalt color of 50 or less as measured by a platinum-cobalt visual comparison method.

5. The method of claim 1, further comprising, after the storing of the washed ion exchange resin in the deionized water, storing the ion exchange resin in phenol for 1 hour or more, followed by dehydrating and drying the washed ion exchange resin.

6. The method of claim 1, wherein a pH of deionized water discharged after the storing of the washed ion exchange resin is 4.18 to 4.29.

7. The method of claim 1, wherein the acidic effluent includes at least one selected from the group consisting of phenol sulfonic acid, sulfobenzoic acid, formyl benzenesulfonic acid, acetyl benzenesulfonic acid, and a sulfonic acid group-containing organic acid.

8. The method of claim 1, wherein the concentration of the acidic effluent is 0.1 ppm to 0.5 ppm.

9. The method of claim 1, wherein the concentration of the acidic effluent is 0.1 ppm to 0.4 ppm.

10. The method of claim 1, wherein the concentration of the acidic effluent is 0.1 ppm to 0.3 ppm.

11. The method of claim 1, wherein the concentration of the acidic effluent is 0.4 ppm to 0.5 ppm.

12. The method of claim 1, wherein the concentration of the acidic effluent is 0.3 ppm to 0.5 ppm.

13. The method of claim 1, wherein the concentration of the acidic effluent is 0.3 ppm to 0.4 ppm.

* * * * *